United States Patent [19]

Kishima et al.

[11] Patent Number: 5,333,494
[45] Date of Patent: Aug. 2, 1994

[54] MATERIAL STRENGTH MEASURING APPARATUS

[75] Inventors: Yoshio Kishima, Saitama; Itsuo Nishiyama, Hyogo, both of Japan

[73] Assignees: Mitsubishi Denki Kabushiki Kaisha, Tokyo; Dainippon Plastics Co., Ltd., Osaka, both of Japan

[21] Appl. No.: 910,438

[22] Filed: Jul. 8, 1992

[30] Foreign Application Priority Data

Sep. 19, 1991 [JP] Japan .................. 3-239060

[51] Int. Cl.$^5$ .............. G01N 3/58; G01N 3/56; G01N 3/40; G01N 33/00
[52] U.S. Cl. .................. 73/104; 73/81; 73/150 R; 73/788
[58] Field of Search ............ 73/104, 150 R, 150 A, 73/78, 7, 8, 866, 856, 81, 83, 85, 783, 788

[56] References Cited

U.S. PATENT DOCUMENTS

| | | | |
|---|---|---|---|
| 2,620,386 | 12/1952 | Alspaugh et al. | 73/104 X |
| 2,625,224 | 1/1953 | Garrett | 73/104 X |
| 3,150,519 | 9/1964 | Heimaster et al. | 73/104 X |
| 3,264,866 | 8/1966 | Bouschart et al. | 73/104 X |
| 3,817,090 | 6/1974 | Michel | 73/104 X |
| 3,827,281 | 8/1974 | Hamel | 73/7 |
| 3,931,732 | 1/1976 | von Heitlinger | 73/104 |
| 4,144,740 | 3/1979 | Beatty | 73/104 X |
| 4,358,974 | 11/1982 | Sakurai | 364/474.17 X |
| 4,485,681 | 12/1984 | Hatamura | 73/862.041 |
| 4,934,185 | 6/1990 | Nishiyama et al. | 73/150 A |
| 5,115,403 | 5/1992 | Yoneda et al. | 73/104 X |

FOREIGN PATENT DOCUMENTS 63-37237 2/1988 Japan .

OTHER PUBLICATIONS

Dr. W. K. Asbeck, "Measuring Coatings Adhesion", *Paint and Varnish Production*, Mar. 1970, pp. 23-30.

*Primary Examiner*—Tom Noland
*Attorney, Agent, or Firm*—Burns, Doane, Swecker & Mathis

[57] ABSTRACT

The present invention relates to a material strength measuring apparatus for specimens having a curved surface or an irregular surface with high accuracy. The measuring apparatus according to the present invention comprises: a supporting stand (1) for fixing a specimen (19) thereon; a guide member (3) fixed on the supporting stand so as to be vertical with respect to the supporting stand; a moving member (26) moving linearly and vertically with respect to a measured surface of the specimen along the guide member; a rotating blade (10) urged toward the measured surface of the specimen; a rotating blade supporting body (8) moving with the moving member linearly and vertically with respect to the measured surface of the specimen; a blade rotating motor (6) fixed to an end of the rotating blade supporting body; elements for forcing the rotating blade into the surface of the specimen; a torque detector (5) for detecting cutting resistance against the rotating blade; a vertical displacement detector (7) fixed to the moving member for detecting vertical displacement of the rotating blade; and a recorder (25) for recording outputs of the torque detector and the vertical displacement detector.

9 Claims, 9 Drawing Sheets

INTERFACIAL CUTTING LENGTH
OF A COATED FILM(mm)

FIG. 12
PRIOR ART

INTERFACIAL CUTTING LENGTH
OF A COATED FILM(mm)

MATERIAL STRENGTH MEASURING APPARATUS

BACKGROUND OF THE INVENTION

1. Field of the Invention

This invention relates to a material strength measuring apparatus, and more particularly to an apparatus for measuring material strength for various materials having a curved surface or an irregular surface through measuring rotational cutting resistance.

2. Description of the Prior Art

Figure 10:
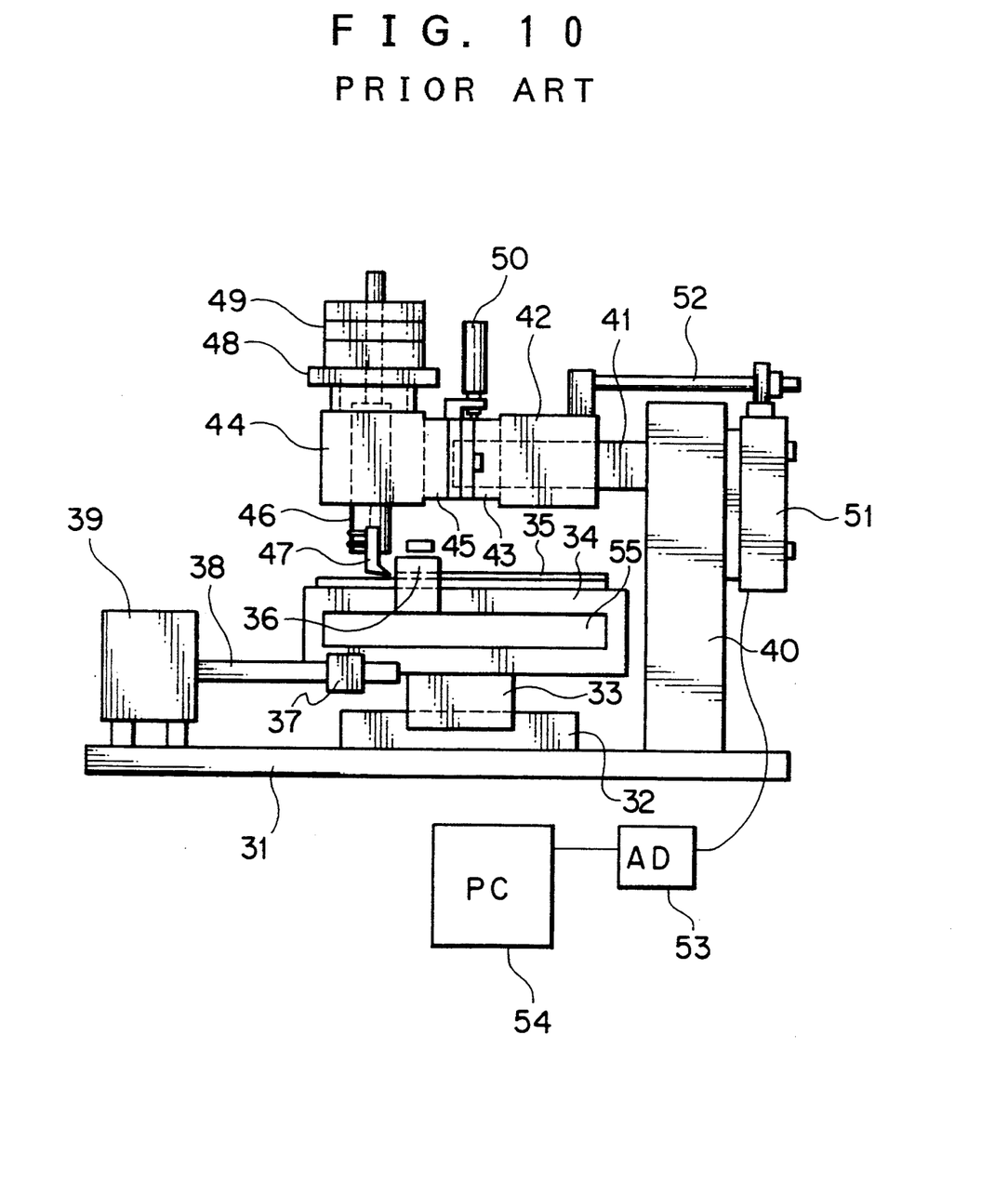
FIG. 10 is a plan view of the conventional apparatus for measuring adhesive strength of a coated film.

FIG. 10 is a front view of a conventional apparatus for measuring adhesive strength of a coated film which is disclosed in Japanese Laid Open Patent Application No. Showa 63-37237 titled "Apparatus for Measuring Adhesive Strength of Coated Film". In the figure, a specimen mounting base 34 is fixed onto a first sliding member 33 which is pivotally mounted on a guide shaft 32 immovably fastened to a supporting stand 31. A coated plate 35 to be a specimen is mounted onto the specimen mounting base 34 by means of a specimen fixing implement 36. A screw-threaded rod 38 is screw-engaged in a nut 37 coupled to the specimen mounting base 34 and an end of the screw-threaded rod 38 is connected to a motor 39. The first sliding member 33 can move linearly in the horizontal direction along the guide shaft 32. A second sliding member 42 slidable moves on and along a guide shaft 41 fixed on the supporting stand 31 through a first connecting member 40. A second connecting member 43 fixed on the second sliding member 42 is connected to a third connecting member 45 fixed on a third sliding member 44, whereby a guide shaft 46 causes the third sliding member 44 to slide up and down. An end of the guide shaft 46 constitutes a supporting body for a cutting blade 47, while the other end thereof forms a screw-threaded rod where a thumb nut 48 for holding the cutting blade and a weight 49 are disposed. The weight 49 functions to adjust and establish the press-contacting force of the cutting blade 47 to the film coated plate 35. A front end portion of a micrometer 50 fixed to the third connecting member 45 is urged to the second connection member 43 in such a manner as to cause the front end portion of the cutting blade 47 to be in parallel with surface of the test specimen material.

A pressure detector 51 fixed on the connecting member 40 detects a repulsive force to be generated against the cutting blade 47 through the second sliding member 42 and the connecting rod 52. Measured data are converted by means of an A/D converter 53, then the A/D converted data are introduced as inputs into a personal computer 45 wherein they are subjected to waveform-processing with use of a Fourier transformation program, power spectra, and a graph of a self-correlation function. A temperature regulator 55 such as a thermo-module is used for adjusting a temperature of the test specimen.

A coated plate having, for example, a length of 150 mm, a width of 70 mm, and a thickness of 1 mm was used as the test specimen 35 and a part of the coated film is peeled off in a size of 2 cm square to expose the surface of the base material. The partially exposed coated plate 35 is mounted on the specimen mounted base 34 by means of the specimen fixing implement 36 in such a manner that it may be tightly attached to the base, and then the cutting blade 47 having a blade width of 4 mm is applied onto the exposed portion of the coated plate 35 and pushed against the coated plate by means of the weight 49 so that a pressing force of 600 gf may be exerted to it. Then, adjustment is made by a micrometer 50 to bring the edge of the cutting blade 47 in parallel with the test specimen.

Then, a motor 39 is driven to shift the coated plate 35 at a velocity of 1 mm/min, while detecting by means of the pressure detector 51 an interfacial cutting resistance to the cutting blade 47 which has been transmitted to it through the connecting rod 52 fixed to the second sliding member 42. At first, a part of the base material is cut in 5 mm length, followed by cutting a part of the coated film in 15 mm length. Then, by use of the thermo-module 55, the temperature of the coated plate is regulated to a constant temperature level ranging from $-10°$ C. to $60°$C.

Figure 11:
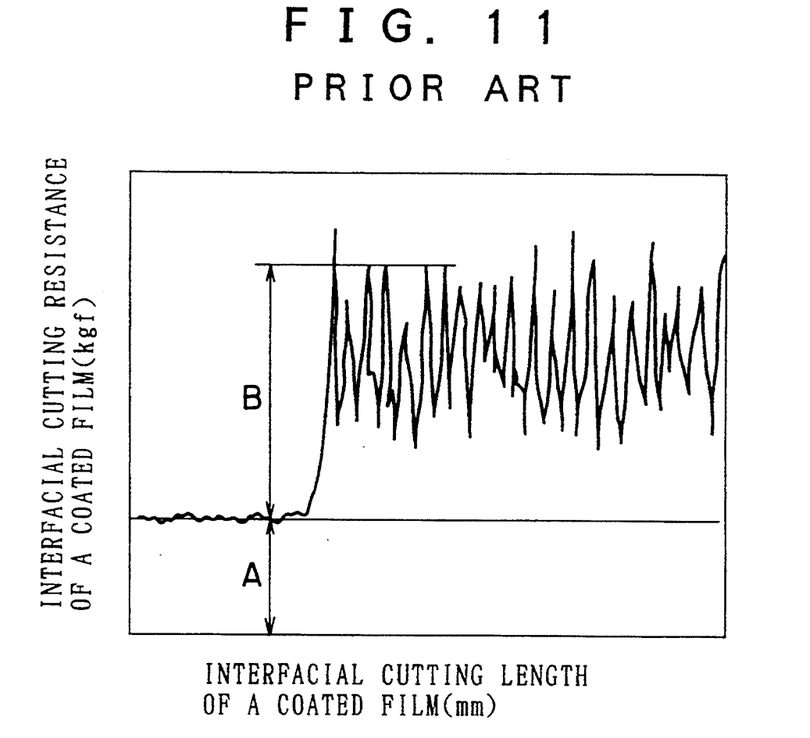
FIG. 11 is a graph showing an example of the relation between interfacial cutting length and interfacial cutting resistance of a coated film.

FIG. 11 is a characteristic diagram showing the cutting resistance to the cutting blade at the interface between the base material and the coated film, in which the ordinate axis denotes the cutting resistance (kg) at an interface between the coated layer and the base material, and the abscissa axis represents a cutting length (mm) of the interface between the coated film and the base material. As seen form the characteristic diagram, the measured data appear in the waveform, in which "A" indicates the cutting resistance of the surface of the base material, and "B" indicates the cutting resistance of the interface between the coated film and the base material.

Figure 12:
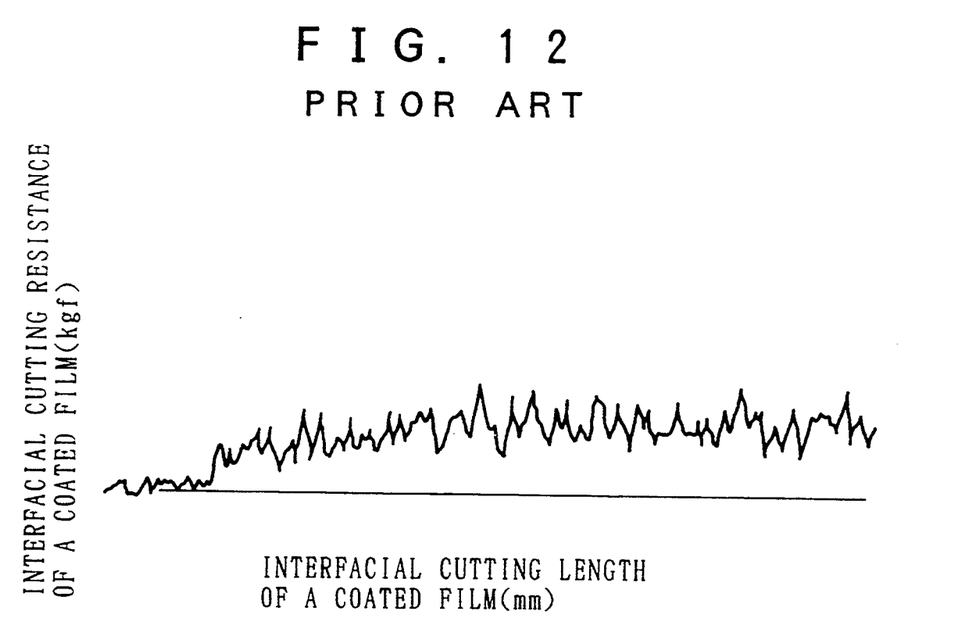
FIG. 12 is the characteristics diagram of the interfacial cutting resistance of the test specimen which has been subjected to the surface preparation of the base material with use of zinc phosphate in acicular crystal.
Figure 13:
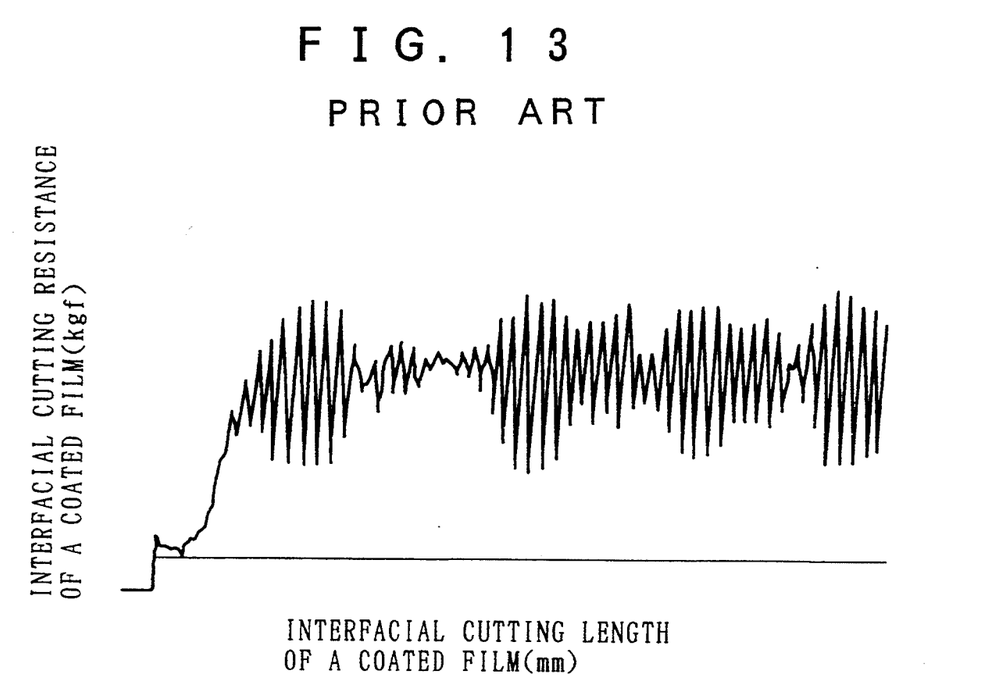
FIG. 13 is the characteristic diagram of the interfacial cutting resistance of the test specimen which has been subjected to the surface preparation of the base material with use of zinc phosphate in columnar crystal.
Figure 14:
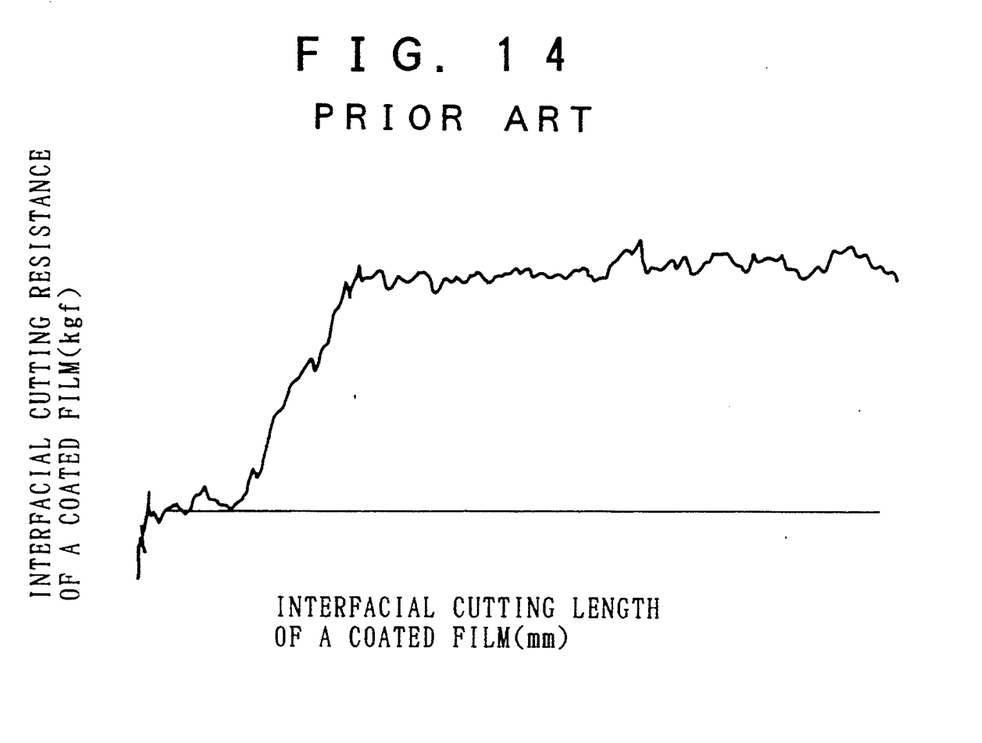
FIG. 14 is the characteristic diagram of the interfacial cutting resistance of the test specimen which has been subjected to the surface preparation of the base material with use of zinc phosphate in scaly crystal.

FIGS. 12 to 14 are graphical representations corresponding to FIG. 11, respectively showing the cutting resistance at the interface in case the conditions for the surface treatment of the base material are varied for coating an epoxy type film by electrical deposition, in which FIG. 12 is the characteristic diagram of the interfacial cutting resistance of the test specimen which has been subjected to the surface preparation of the base material with use of zinc phosphate in acicular crystal; FIG. 13 is the characteristic diagram of the interfacial cutting resistance of the test specimen which has been subjected to the surface penetration of the base material with use of zinc phosphate in columnar crystal; and FIG. 14 is the characteristic diagram of the interfacial cutting resistance of the test specimen which has been subjected to the test specimen which has been subjected to the surface preparation of the base material with use of zinc phosphate in scaly crystal. It will be seen from these characteristic diagrams that, even when the coated film is of the same material, if the formation treatment of the treated steel plate differs, the adhesive strength of the coated film differs accordingly with the consequence that the interfacial cutting resistance and the waveform become varied as shown in FIGS. 12 to 14.

Figure 15:
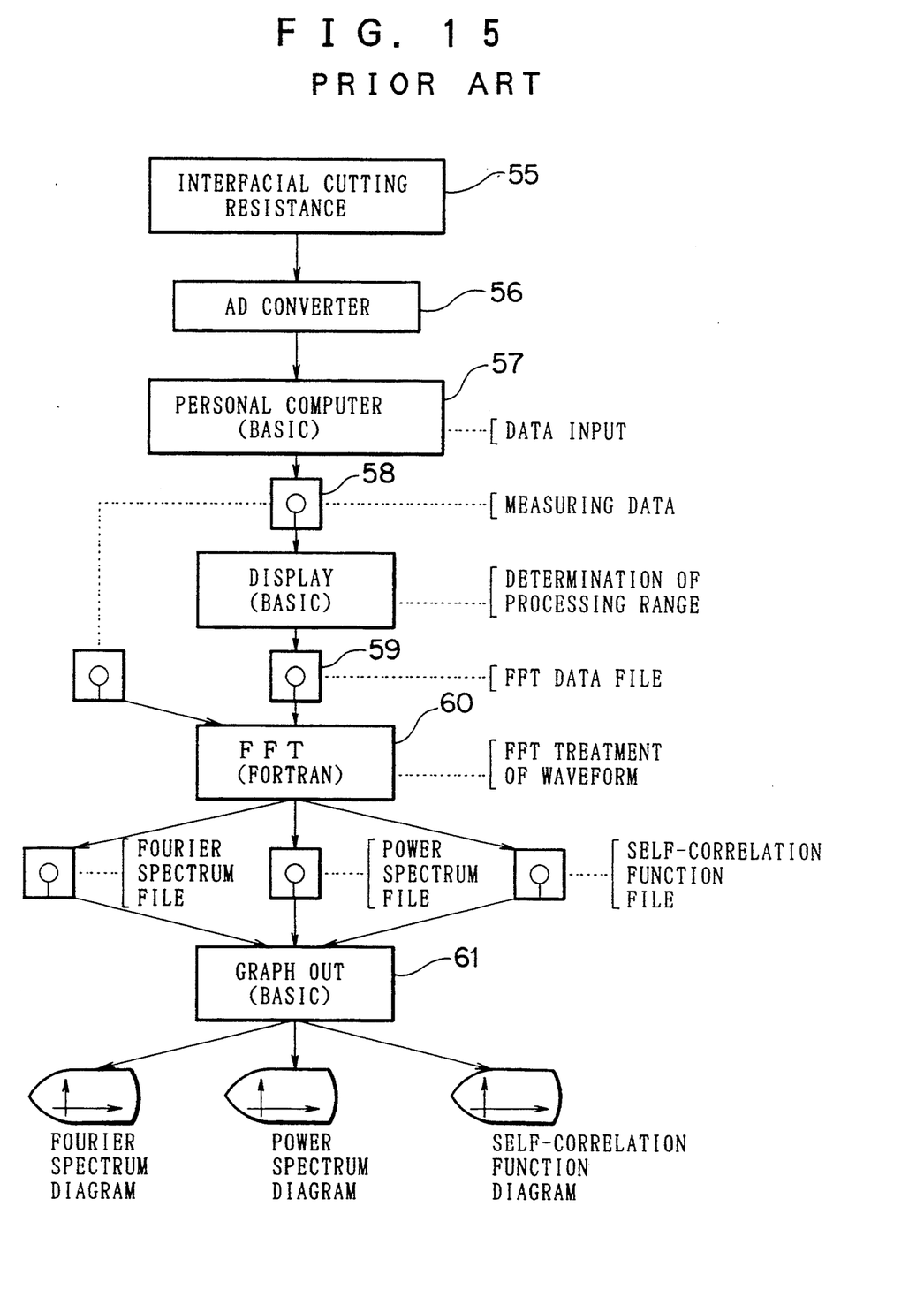
FIG. 15 is a flowchart of a program for waveform-processing.

FIG. 15 is a flow chart for the wave form analysis program, in which the measured data 55 of the interfacial cutting resistance is processed by the A/D converter 56, input into the personal computer 57, and output to a program file 58. After producing the output data of the program file 58 in the form of a graph, a processing range is input by a cursor from the image plane, followed by processing 60 of the measured data by use of the subsequent Fourier conversion program 59 to output the result of the conversion into the film.

Then, the input is introduced into the respective files of Fourier spectra, power spectra and self-correlation function, from which graphs are output at 61.

Figure 16:
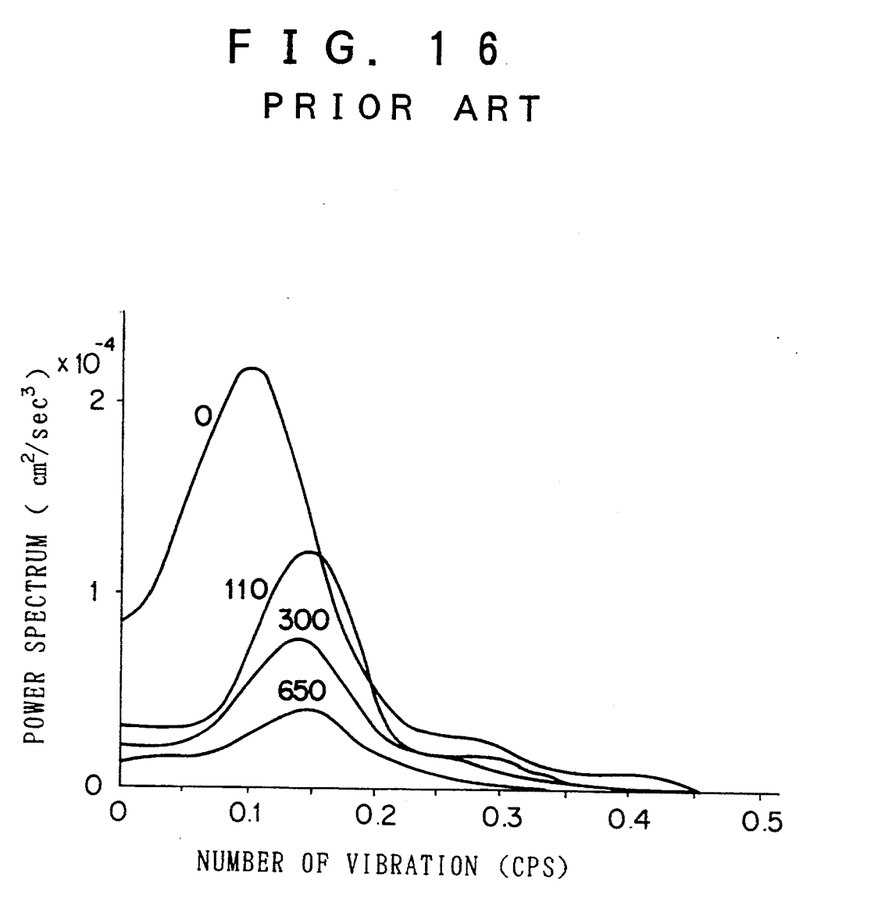
FIG. 16 is a power spectral diagram to be obtained by the Fourier conversion of the interfacial cutting resistance of a urethane type coating material.

FIG. 16 is a power spectral diagram to be obtained by the Fourier conversion of the interfacial cutting resistance of a urethane type coating material for each heating time of 0 hr., 100 hrs., 300 hrs., and 650 hrs.. In this graphical representation, the abscissa represents the number of vibration (cps) and the ordinate denotes power spectrum ($cm^2/sec^3$). From this graph, it will be seen that, in the heat-resistance test at 160° C., the power spectrum tends to lower while the peak number of vibration tends to increase as the heating time becomes prolonged.

The interfacial cutting resistance is a composition force of the adhesive strength of the coated film and the material strength, the breaking form of which is recorded as a waveform. By subjecting the measured values of the interfacial cutting resistance to the Fourier conversion and then carrying out the waveform analysis, there can be obtained information for clarifying the nature of the phenomenon.

By the way, in the above-described conventional device for measuring the adhesive strength of the coated film, explanation has been made as to an instance of using a general coated plate having a film thickness of a few tens of micrometers or above. It may, however, be feasible that film be coated on a plastic plate to obtain the same effect as in the above-mentioned conventional example.

With the above-described conventional apparatus for measuring adhesive strength of a coated film, it was necessary to provide the coated plate (35) for the film testing purpose and to analogize the adhesive strength of the coated film of the object to be tested on the basis of this result of measurement, hence there remained problems with respect to reliability and precision of the result of the measurement of analogy.

There was also a problem such that the shape of the specimen must be flat and specimens having curved surface or an irregular surface can not be tested since the specimen moves linearly during the test.

SUMMARY OF THE INVENTION

The present invention has been accomplished to avoid the above drawbacks, and therefore it is an object of the present invention to provide a material strength measuring apparatus in which the material strength of material directly sampled at a site as well as specimen for measurement can be measured and not only specimen having a flat surface but also a curved surface and an irregular surface can be tested.

To achieve the above objective, the material strength measuring apparatus according to the present invention comprises: a supporting stand for fixing a specimen thereon; a guide member fixed on the supporting stand so as to be vertical to the supporting stand; a moving member moving linearly and vertically to a measured surface of the specimen along the guide member; a rotating blade urged to the measured surface of the specimen; a rotating blade supporting body moving with the moving member linearly and vertically to the measured surface of the specimen; a rotation blade rotating means fixed to an end of the rotating blade supporting body; an urging force adjusting means for adjusting the urging force of the rotating blade to the measure surface of the specimen; a torque detector for detecting cutting resistance against the rotating blade; a vertical displacement detector fixed to the moving member for detecting vertical displacement of the rotating blade; and a recording means for recording outputs of the torque detector and the vertical displacement detector.

Further, another material strength measuring apparatus according to the present invention comprising: a fixed member fixed to a specimen; a guide member fixed to the fixed member so as to be vertical with respect to the fixed member; a moving member moving linearly and in parallel with a measured surface of the specimen along the guide member; a rotating blade urged to the measured surface of the specimen; a rotating blade supporting body for supporting the rotating blade at an end thereof, the rotating blade supporting body moving with the moving member linearly and vertically to the measured surface of the specimen; a rotation blade rotating means fixed to an end of the rotating blade supporting body; an urging force adjusting means for adjusting urging force of the rotating blade to the measure surface of the specimen; a traveling means for traveling the moving member; a torque detector for detecting cutting resistance against the rotating blade; a vertical displacement detector fixed to the moving member for detecting vertical displacement of the rotating blade; and a recording means for recording outputs of the torque detector and the vertical displacement detector.

In the material strength measuring apparatus according to the present invention, the specimen is fixed to the supporting stand to rotate the rotating blade while being urged to the measured surface of the specimen and then the rotation torque against the rotating blade is detected and the displacement of the rotating blade in the direction that the rotating blade proceeds is simultaneously detected, which directly provides material strength in the direction that the rotating blade proceeds.

Further, in another material strength measuring apparatus according to the present invention, the fixed member which is fixed to the specimen is provided, permitting strength of material on the site as well as specimens for measurement to be directly measured at the site.

BRIEF DESCRIPTION OF THE DRAWINGS

The present invention will be more apparent from the ensuring description with reference to the accompanying drawing wherein.

DETAILED DESCRIPTION OF PREFERRED EMBODIMENTS

Now, a material strength measuring apparatus according to the present invention will be explained with reference to the drawings.

Figure 1:
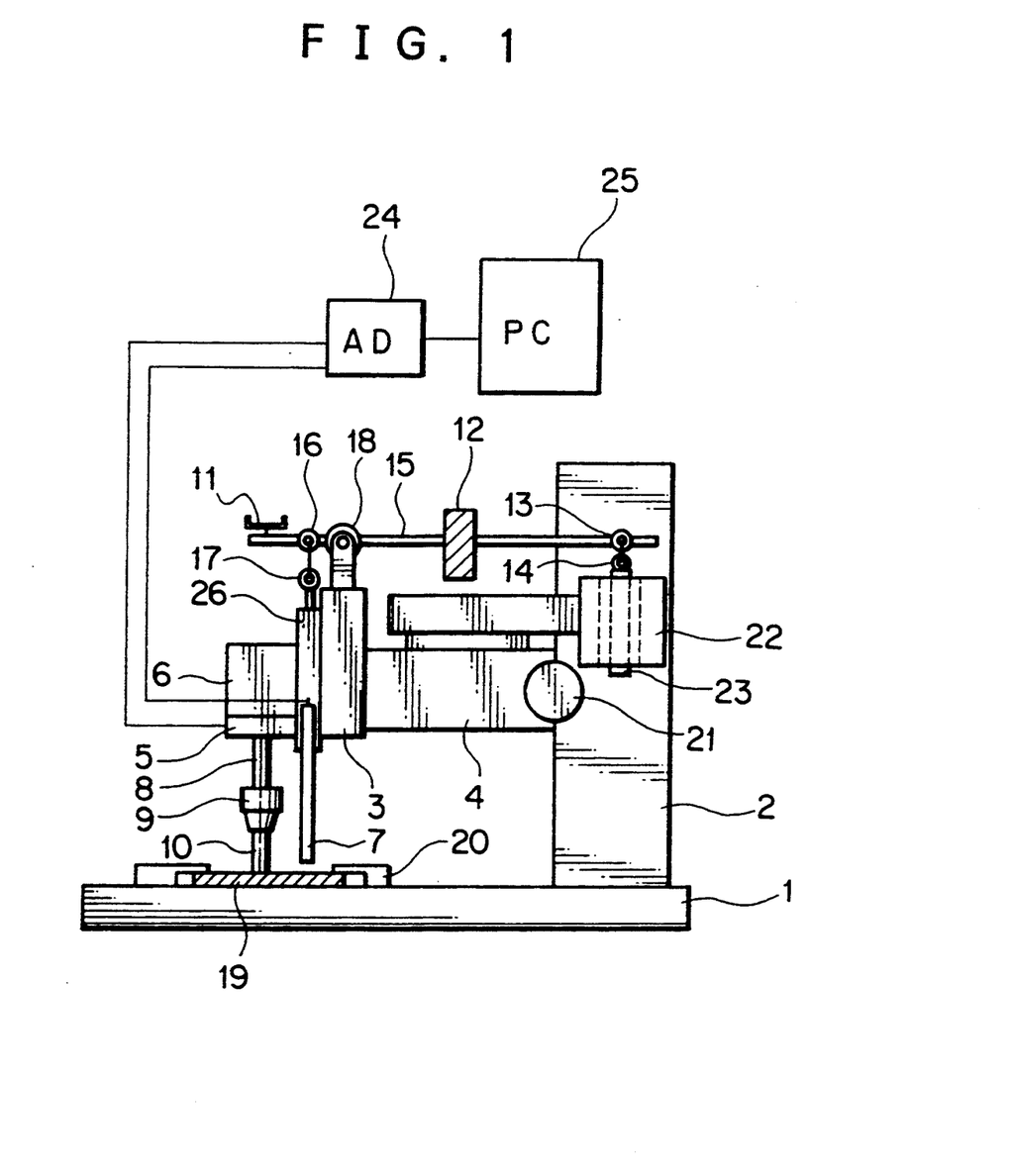
FIG 1. shows a front view of a material strength measuring apparatus according to an embodiment of the present invention.

FIG. 1 is a front view of the material strength measuring apparatus according to an embodiment of the present invention.

In the figure, a moving member 26 is fixed to a guide shaft 3 as a guide member. The guide shaft 3 is supported by way of connecting members 4 and 2 on a supporting stand so as to be vertical with respect to the stand. A motor 6 for rotating a rotating blade described below and a torque meter 5 for detecting the cutting resistance against the rotating blade are fixed on a side of the moving member 26. Further, on an end of the moving member 26 is fixed a first miniature bearing 17 and on the other end a sound film thickness meter 7 is fixed to detect vertical displacement of the rotating blade. A supporting point of a balancing rod 15 is formed as a second miniature bearing 18, which is fixed on an end of the guide shaft 3. On an end of the balancing rod 15 is fixed a third miniature bearing 16 and the weight stand 11 and the third miniature bearing 16 are connected to the first miniature bearing 17 with a connecting rod. On the balancing rod 15 is movably mounted a weight 12 to adjust the balance of the balancing rod 15. Further, on the other end of the balancing rod 15 is mounted a movable shaft 23 of an electromagnetic force balance 22 by way of miniature bearings 13 and 14. The force balance is fixed on the connecting member 4.

The rotating blade 10 is removably mounted to an end of a motor shaft 8. A specimen 19 is fixed on the supporting stand by a fixing means 20. Denoted 9 is a connecting means for the rotating blade.

Figure 6:
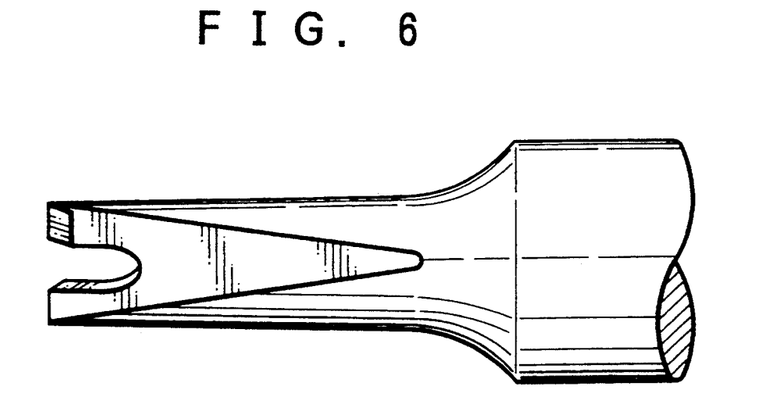
FIG. 6 is a schematic side view of the rotating material strength measuring apparatus according to further embodiment of the present invention.
Figure 7:
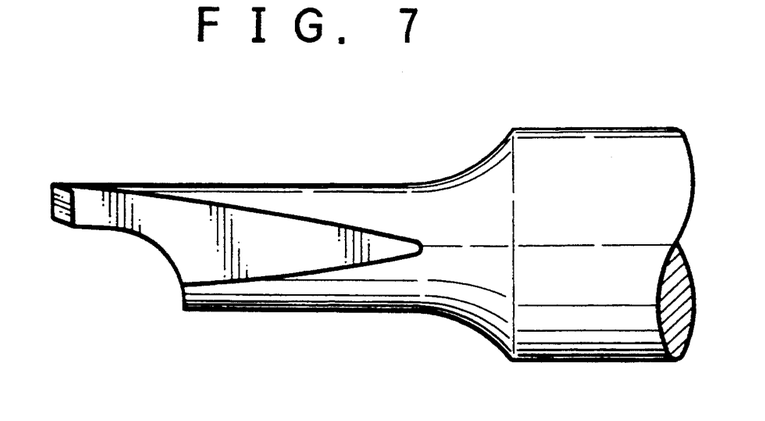
FIG. 7 is a schematic side view of the rotating material strength measuring apparatus according to further embodiment of the present invention.

In order to simplify the cutting mechanism, a flat drill with a notch at a center portion of tip thereof shown in FIG. 6 and another flat drill, from which, a half tip portion thereof shown in FIG. 7 is removed, are selected.

The cutting operation of the rotating blade to the specimen 19 is performed by the motor 6 under the conditions that electric current of the force balance is set at a predetermined value; a prescribed weight is put on the weight stand 11; and the rotating blade 10 is urged toward the specimen 19. The rotation speed of the rotating blade is not limited to a certain range in the present invention, but, it may preferably be adjusted between 60 rpm and 0.06 rpm to prevent heat generation at the cutting operation.

The cutting operation with the rotating blade 10 can be performed under the condition of uniform urging force of the rotating blade toward the measuring surface of uniform cutting speed. In the present invention, both conditions can be applied to the measuring apparatus.

The cutting resistance against the rotating blade 10 is detected by the torque meter 5 and the vertical displacement of the rotating blade, that is, the cutting depth is detected by the sound film thickness meter 7.

Data measured by the torque meter 5 and the sound film thickness meter 7 are A/D converted by an A/D converter 24 to be input to a personal computer 25, which outputs a graph showing the relation between the cutting depth and the rotating torque. As a result, material strength can be obtained by the gradient of a line showing the relation between the depth and the torque.

In the material strength measuring apparatus with the structure described above, the operation procedure of the apparatus when a polystyrene plate is tested as the specimen 19 will be explained. At first, the polystyrene plate is fixed on the supporting stand 1. Then the rotating blade 10 of a flat drill having a diameter of 1 mm is urged to the surface of the plastic plate 19. Under these conditions, zero point adjustment of the sound film thickness meter 7 is carried out. When the load of the rotation blade is set at 500 gf and the rotation speed thereof 100 rpm, the rotation blade proceeds into the plastic plate.

Figure 8:
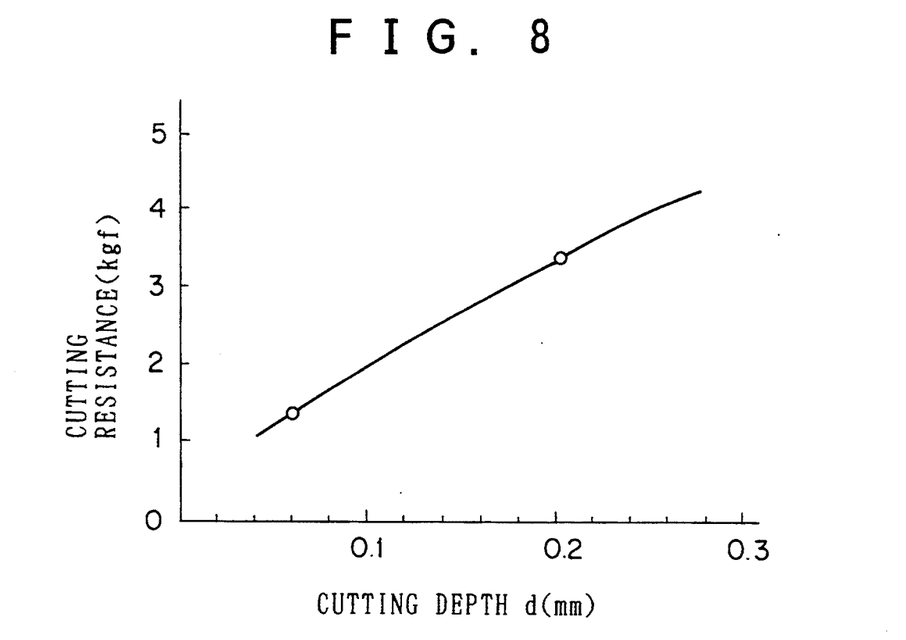
FIG. 8 is a graph showing an example of the relation between film thickness and rotation torque in the test with the material strength measuring apparatus according to the present device.

FIG. 8 shows a graph which is obtained by a test using the material strength measuring apparatus according to the present invention. The graph shows a rotation torque as cutting resistance to cutting depth of the rotating bade. In the figure, the ordinate axis denotes the rotation torque P and the abscissa axis represents a cutting depth.

Figure 2:
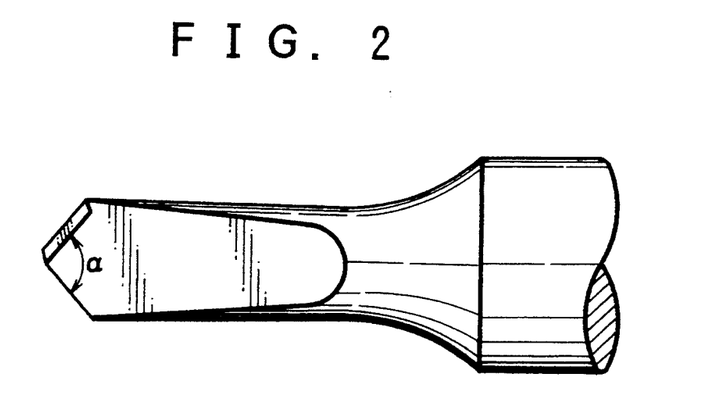
FIG. 2 is a schematic side view of a rotating blade of the material strength measuring apparatus according to an embodiment of the present invention.
Figure 3:
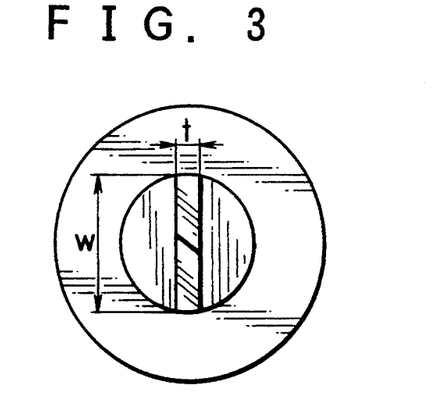
FIG. 3 is a schematic front view of the rotating blade of FIG. 2.
Figure 4:
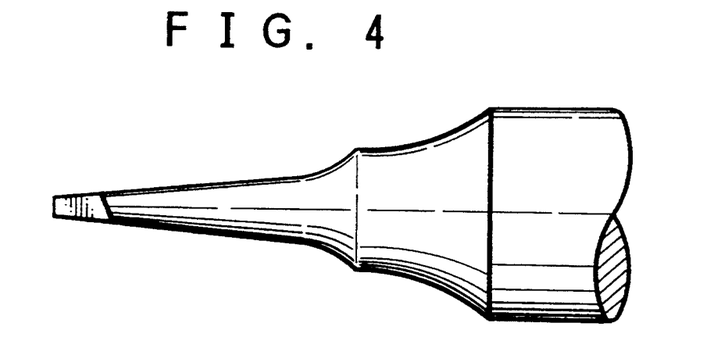
FIG. 4 is a schematic plan view of the rotating blade of FIG. 2.

FIG. 2 shows a schematic side view of the flat drill described above. FIGS. 3 and 4 are schematic front and plan views of the flat drill of FIG. 2. The flat drill in FIGS. 2 to 4 has a blade width (w) of 1 mm, a thickness (t) of 0.2 mm, and a tip angle ($\alpha$) is 100°.

Figure 5:
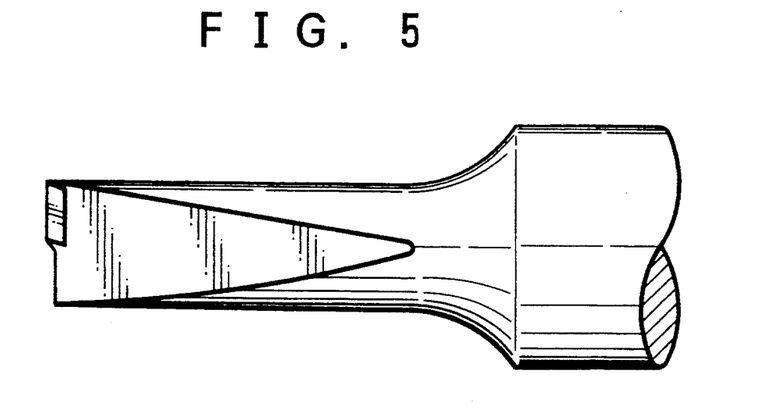
FIG. 5 shows a schematic side view of the rotating blade of the material strength measuring apparatus of FIG. 4.
Figure 9:
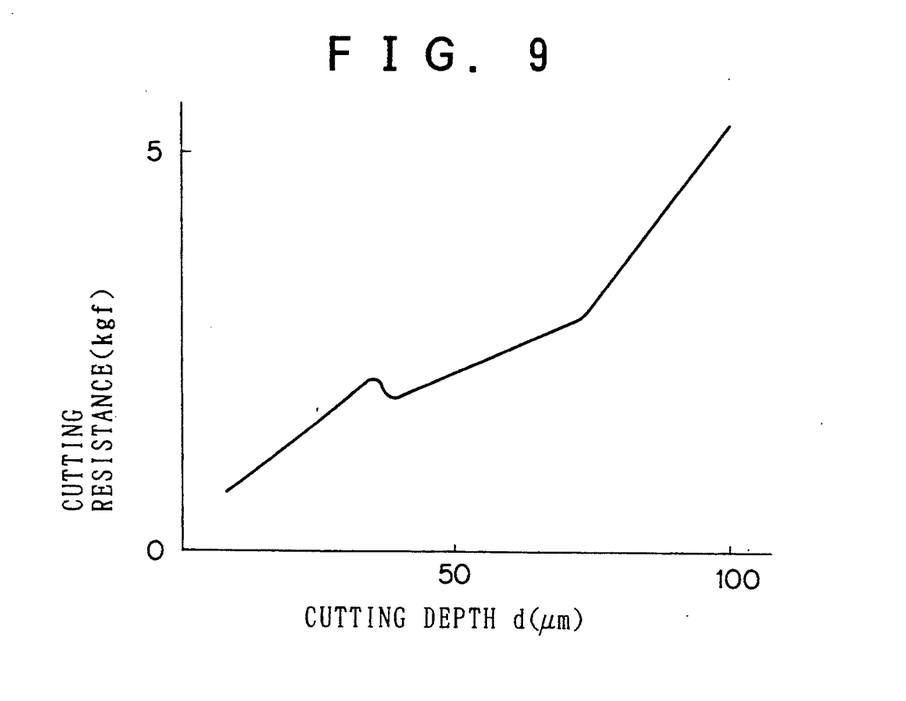
FIG. 9 is a graph showing another example of the relation between film thickness and rotation torque in the test with the material strength measuring apparatus according to the present device.

FIG. 9 is a graph showing measuring result of a multi-layer film. A first layer from outside is a melamine-alkid coated film of a thickness of 30 $\mu$m, a second layer an epoxy coated film of a thickness of 40 $\mu$m, and a third layer a cation electrodeposition coated film of a thickness of 30 $\mu$m. FIG. 9 is a graph showing the test result when the above specimen is tested by a flat drill having a linear tip. The tendency of the strength for each layer can be obtained from the graph. FIG. 5 shows a schematic side view of a flat drill with a tip angle of 180°.

As described above, with the material strength measuring apparatus according to the present invention, the material strength of a single layer or multi-layer coated film, plastic material, and composite is tested and relatively compared through the same measuring method by simple operation procedure with high accuracy. In the above embodiment, the force balance 22 and the weight are used to urge the rotating bade 10 toward the specimen 19. A spring, oil pressure, or air pressure may be used for the same purpose.

As the rotating blade 10, drills generally used as well as the flat drill shown in FIGS. 2 to 5 may be used. A well-known strain meter may be used as a torque meter. Although the motor 6 is an ordinary motor, a stepping motor is preferably used to control the rotation speed thereof.

Further, since bearing mechanism comprising a guide shaft and sliding member 26 affects the torque of the rotating blade and the measuring accuracy of the cutting depth, the mechanism with little or no play is preferably used.

In the embodiment described above, the sound film thickness meter is used as a vertical displacement detector to detect vertical displacement of the rotating blade, but a differential transformer or noncontacting-type detector with a laser may be used.

The specimen can be fixed on the supporting stand by magnets or a jig for grasping such as a vise. In such a case, the supporting stand is provided with a hole through which the rotating blade proceeds to cut the specimen. Since the specimen is fixed on the stand with fixed members, the property of coated films can be measured directly at the site, resulting in improved accuracy and reliability.

As described above, in the material strength measuring apparatus according to the present invention, the specimen is fixed on the supporting stand, and the rotation torque against the rotating blade is measured when the rotating blade is rotated with the rotating blade being urged on the measured surface of the specimen, and simultaneously, the displacement of the rotating blade in the direction that the rotating blade proceeds is detected. Therefore, specimens may be measured regardless of curved surface or irregular surface of the measured surface.

Further, in another embodiment of the present invention, the supporting stand is fixed to a specimen by the magnets, in addition to the above effects, material at the site can directly be measured at the site.

What is claimed is:

1. A material strength measuring apparatus for measuring strength of a material comprising:
    a supporting stand for fixing a specimen thereon, said specimen being made from at least said material;
    a guide member fixed on said supporting stand so as to be vertical with respect to said supporting stand;
    a moving member moving linearly and vertically with respect to a measured surface of said specimen along said guide member;
    a rotating blade urged toward said measured surface of said specimen;
    a rotating blade supporting body moving with said moving member linearly and vertically with respect to said measured surface of said specimen;
    a rotating blade rotating means fixed to an end of said rotating blade supporting body;
    an urging force adjusting means for adjusting an urging force of said rotating blade toward said measured surface of said specimen;
    a torque detector for detecting cutting resistance against said rotating blade;
    a vertical displacement detector fixed to said moving member for detecting vertical displacement of said rotating blade; and
    a recording means for recording outputs of said torque detector and said vertical displacement detector to indicate the strength of said material.

2. A material strength measuring apparatus as claimed in claim 1, wherein said outputs of said torque detector and said vertical displacement detector are processed by a computer to display changes in material strength of portions from the measured surface to inner portions of said specimen.

3. A material strength measuring apparatus as claimed in claim 1 or 2, wherein rotation speed of said rotating blade is between 60 rpm and 0.06 rpm.

4. A material strength measuring apparatus as claimed in claim 1, wherein said rotating blade includes a flat drill with a notch at a center portion of a tip thereof.

5. A material strength measuring apparatus as claimed in claim 1, wherein said rotating blade includes a flat drill with a half tip portion thereof removed.

6. A material strength measuring apparatus as claimed in claim 1, wherein material strength of said specimen is determined by a gradient of a line showing a relation between cutting depth and torque against the rotating blade.

7. A material strength measuring apparatus as claimed in claim 1, wherein a uniform urging load of said rotating blade is applied to said measured surface of said specimen.

8. A material strength measuring apparatus as claimed in claim 1, wherein a uniform cutting speed of said rotating blade is used to cut said measured surface of said specimen.

9. A material strength measuring apparatus for measuring strength of a material comprising:
    a fixed member fixed to a specimen, said specimen being made from at least said material;
    a guide member fixed to said fixed member so as to be vertical with respect to said fixed member;
    a moving member moving linearly and in parallel with a measured surface of said specimen along said guide member;
    a rotating blade urged toward said measured surface of said specimen;
    a rotating blade supporting body for supporting said rotating blade at an end thereof, said rotating blade supporting body moving with said moving member linearly and vertically with respect to said measured surface of said specimen;
    a rotation blade rotating means fixed to an end of said rotating blade supporting body;
    an urging force adjusting means for adjusting an urging force of said rotating blade toward said measured surface of said specimen;
    a traveling means for traveling with said moving member;
    a torque detector for detecting cutting resistance against said rotating blade;
    a vertical displacement detector fixed to said moving member for detecting vertical displacement of said rotating blade; and
    a recording means for recording outputs of said torque detector and said vertical displacement detector to indicate the strength of said material.

* * * * *